United States Patent
Korpan et al.

(10) Patent No.: US 7,713,186 B2
(45) Date of Patent: May 11, 2010

(54) DETECTION AND INFLUENCING OF PHYSIOLOGICAL AND/OR PATHOLOGICAL STATES

(76) Inventors: Nikolai Korpan, Lazarettgasse 31/5, A-1090 Vienna (AT); Juri A. Filippov, Mechnikovastrasse 7/8, 320070 Dnipropetrovsk (UA)

( * ) Notice: Subject to any disclaimer, the term of this patent is extended or adjusted under 35 U.S.C. 154(b) by 995 days.

(21) Appl. No.: 10/553,782

(22) PCT Filed: Apr. 22, 2004

(86) PCT No.: PCT/AT2004/000134

§ 371 (c)(1),
(2), (4) Date: Dec. 7, 2005

(87) PCT Pub. No.: WO2004/093992

PCT Pub. Date: Nov. 4, 2004

(65) Prior Publication Data

US 2007/0015950 A1    Jan. 18, 2007

(30) Foreign Application Priority Data

Apr. 24, 2003    (AT) ................................ A 625/2003

(51) Int. Cl.
*A61N 2/12* (2006.01)
*A61N 2/00* (2006.01)
(52) U.S. Cl. ........................................................ 600/9
(58) Field of Classification Search .............. 600/9–15; 310/156.01, 152, 171
See application file for complete search history.

(56) References Cited

U.S. PATENT DOCUMENTS

| | | | | |
|---|---|---|---|---|
| 4,936,305 A | * | 6/1990 | Ashtiani et al. | 607/57 |
| 5,545,017 A | * | 8/1996 | Strohl et al. | 417/423.7 |
| 6,001,055 A | * | 12/1999 | Souder | 600/9 |
| 6,210,317 B1 | * | 4/2001 | Bonlie | 600/9 |
| 2002/0115903 A1 | * | 8/2002 | Miyazaki | 600/9 |
| 2003/0092960 A1 | * | 5/2003 | Holcomb | 600/9 |
| 2005/0065394 A1 | * | 3/2005 | Spiegel | 600/9 |

FOREIGN PATENT DOCUMENTS

| | | |
|---|---|---|
| EP | 0 838 236 | 4/1998 |
| EP | 1 287 852 | 3/2003 |
| FR | 2 210 420 | 7/1974 |
| RU | 2 180 603 | 2/2000 |
| WO | 99/39769 | 8/1999 |

OTHER PUBLICATIONS

Abstract of RU 2121383, May 2005, entitled "Device for Therapeutic Exposure of Man's Internal Tissues to MagneticField."

* cited by examiner

*Primary Examiner*—Charles A Marmor, II
*Assistant Examiner*—Catherine E. Burk
(74) *Attorney, Agent, or Firm*—Dykema Gossett PLLC

(57) ABSTRACT

A device for detecting and influencing the physiological and/or pathological state of the human or animal body, including a housing which has a first housing wall that, in turn, has an outer surface provided for placing against a body to be treated. A rotor is situated inside the housing and is rotationally driven about an axis that is essentially perpendicular to the first housing wall. First magnets are mounted on the rotor, and their magnetic fields are oriented in the same direction that is parallel to the rotation axis. At least one additional magnet is situated essentially coaxial to the rotation axis with a polarity of each being oriented in an opposite direction to the first magnets.

9 Claims, 3 Drawing Sheets

DETECTION AND INFLUENCING OF PHYSIOLOGICAL AND/OR PATHOLOGICAL STATES

BACKGROUND OF THE INVENTION

1. Field of the Invention

The invention relates to an apparatus for detecting and influencing the physiological and/or pathological state of the human or animal body, comprising a housing which has a first housing wall which, in turn, has an outer surface provided for placing against the body to be treated, with a rotor being situated inside the housing and being rotationally driven about an axis which is essentially perpendicular to the first housing wall, and with first magnets being arranged on the rotor whose magnetic fields are oriented in the same direction which is parallel to the rotational axis.

2. The Prior Art

Various apparatuses have become known to influence the human body by application of electromagnetic fields. Partly these are diagnostic devices such as nuclear spin tomography, and partly other therapeutic applications are concerned.

An apparatus has become known in order to measure the biological state of a patient by measuring radiated waves in the millimeter range. Such methods have been published for example in: Devyatkov N. D., Golant M. V., "About outlooks of usage of electromagnetic radiations of a millimetre wave in quality of high-informative means of obtaining of data about specific processes in alive organisms" in Letters to Journal of Technical Physics, 1986; 12 (5): 288-291.

Such a direct measurement of the radiation intensity is difficult as a result of the very low amplitudes and requires a complex set-up of apparatuses. The practical application of such methods is therefore very limited.

Further known diagnostic methods try to obtain findings in a non-invasive manner such that the frequency and periodicity of fundamental physiological processes are measured. This can concern the breathing rhythm or the heart rhythm or pulse beat. In the course of such measurements the body to be examined can be loaded with high-frequency waves in order to obtain additional information. Certain diagnoses can be made in this manner, but it is not possible to detect brain activity in a suitable manner.

Magneto-acoustic apparatuses for the non-invasive measurement of bioelectric currents in the brain have become known (Towe B. C., Islam M. R.: "A magneto-acoustic device for the non-invasive measurements of bioelectric currents"; IEEE Trans. Biomed. Eng. 1988; 35(10): 892-894; Spiegel R. I. e.a. Measurements of small mechanical vibration of brain tissue exposed to extremely low-frequency electric fields; Bioelectromagnetic, 1986; 7(3): 295-306). Such non-invasive magneto-acoustic measurements can lead to a large quantity of information on individual organs and systems of the body, on the basis of performance under strain of the organism with a variable electromagnetic field. The acoustic oscillations lead to the origination of a potential difference at the boundary surfaces between the individual media with different acoustic properties (Debye potential) which is comparable with the membrane potential of a large number of cells, so that this method cannot be designated as entirely non-invasive. Disturbances occur as a result of thermo-elastic changes in tissue, and the brain in particular, which distort the measurements.

A therapeutic appliance is further known from RU 2 180 603C in which rotating magnetic fields are used in order to influence the human body. In addition, electric voltages are applied to the skin via electrodes. It has been noticed however that the overall effect does not go beyond a limited range. Further magnetic apparatuses for treating the body are described in WO 99/39769 and in RU 2 121 383 C. Similar disadvantages occur in these cases too.

It is the object of the present invention to avoid such disadvantages and to provide an apparatus which can be used for diagnostic purposes as well as for therapeutic purposes and which is capable of exerting a strong and reproducible effect on the body in a non-invasive manner.

The objects are achieved in such a way that at least one further magnet is arranged substantially coaxially to the rotational axis, which magnet is oriented in an opposite direction relative to the first magnets.

In the application of the apparatus in accordance with the invention in the diagnostic field, reference is hereby made to a method which is similar in respect of concept and technical sense which is known as the Voll method and has been published in Leonhardt H.: "Fundamentals in Electro Puncture according to Voll." ML-Verlag GesmbH, Hetzen, 1980. The idea of this method and this apparatus is defining a continuously monitored parameter which allows a differentiation between the reactions of a healthy and sick person. In a technical respect, the Voll method consists of the definition of the electric conductivity in various segments of a body meridian and the examination of the dynamics in predetermined points of the body. The measuring range is mapped to a scale of between 0% and 100%, with the middle point of the scale corresponding to a normal value, the upper end of the scale indicating inflammation illnesses and the lower end of the scale indicating degradation of the tissue. The application of the Voll method is made difficult by a number of technical and organizational difficulties. A major source of errors is the correct application of the electrodes at predetermined points on the body because slight local changes, the geometry of the electrode, the applied pressure and other parameters have a relatively strong influence on the result. Moreover, notice must be taken from a cybernetic viewpoint that the predetermined body parts to be examined represent time-changeable, non-linear dynamic objects (Croley T. E.: "Electrical Acupuncture Point Conductance in the Compared to that in the Dead, Amer. J. Acupunct., 1986; 14(1): 57-60), so that the results of the diagnosis can represent only the momentary energy state of the body under the influence of external factors without allowing reliable statements on the actual fundamental state of the organism.

The apparatus of the present invention allows subjecting the body in a precisely defined manner to an electromagnetic field which allows obtaining measured values in a robust and reliable manner in order to diagnose the state of the body. The place of the application and the variation of the rotational speed or the frequency of the changes of the rotational direction allow influencing and changing the measured values which are obtained in the known manner via electrodes which are attached to the body. Conclusions can be drawn from the manner of influencing which allows obtaining reliable diagnoses.

A relevant aspect of the invention is opposite polarization of the central further magnet in relationship to the rotating first magnets. This means that either the magnetic north pole of the central further magnet faces towards the first housing wall and the magnetic south poles of the first magnets face towards the housing wall, or vice-versa. As a result of this special arrangement, it is possible that the magnetic field which penetrates the body can be aligned towards individual organs in an especially purposeful manner. The first housing wall is made of a magnetically neutral material such as plastic and is provided with the thinnest possible configuration in order to reduce losses as far as possible. Strong magnets are preferably used as magnets which preferably develop a field strength of between 0.5 T and 5 T.

An especially simple configuration of the apparatus in accordance with the invention is obtained when the magnets are configured as permanent magnets. In order to allow reaching the above field strength in a secure and reliable way, it is especially preferable when the magnets are made of a neodym iron boron alloy or of a praseodym iron boron alloy. Such so-called SE-magnets on the basis of rare earths come with especially advantageous properties in connection with the present invention. As an alternative to this it is also possible to configure the magnets partly or completely as electromagnets. The supply of such electromagnets on the rotor can be provided in this case via slip rings for example.

The suitable selection of the speed of the rotor (angular velocity) and optionally the periodic changing of the rotational direction with a certain base frequency may allow a purposeful influencing of the human and animal body. This allows not only obtaining precise diagnostic information in the course of measurements performed simultaneously, but therapeutic treatments can also be performed. Such treatments allow treating illnesses for example which are illustrated and classified on a seven-stage scale of the energy-informative system of the patient. In such a classification, the seventh stage represents the state of health, whereas the lower stages define different stages of illnesses. A threshold value is usually assumed between the second and the third stage below which convalescence is regarded as impossible. The application of the present apparatus in accordance with the invention allows bringing a patient from the third, fourth, fifth or sixth stage to the seventh stage. Double-blind studies performed on a large number of patients have proven the effectiveness of the apparatus in accordance with the invention.

In a preferred embodiment of the invention it is possible that the further magnet is attached in a stationary manner to the housing. This allows an especially simple configuration of the apparatus from a mechanical viewpoint, with said further magnet being attached directly to the first housing wall for example. It is also possible alternatively that the further magnet is attached to the central region of the rotor. The further magnet is thus not stationary, but the magnetic field produced by this magnet is quasi stationary especially in a central symmetrical configuration of the further magnet.

It has proven to be especially advantageous when the first magnets are attached in regions of radial rays of the rotor which have even angular distances. In this manner, a magnetic field can be produced which revolves with an even angular velocity. The angular velocity can be adjusted accordingly depending on the respective purpose. The arrangement of the first magnets on three rays is especially preferable, so that the angular distances are 120° each. In the simplest of cases, one magnet can be arranged along each ray. In the case of applications over larger surface areas it is preferable when several magnets are arranged on each ray.

It has proven to be especially advantageous when the first magnets and the further magnet comprises pole faces which are situated in a common plane and border the first housing wall directly. An especially even influence of the magnetic field on the tissue is thus achieved.

The present invention is explained in closer detail by reference to embodiments shown in the drawings.

DETAILED DESCRIPTION OF THE PREFERRED EMBODIMENTS

Figure 1:
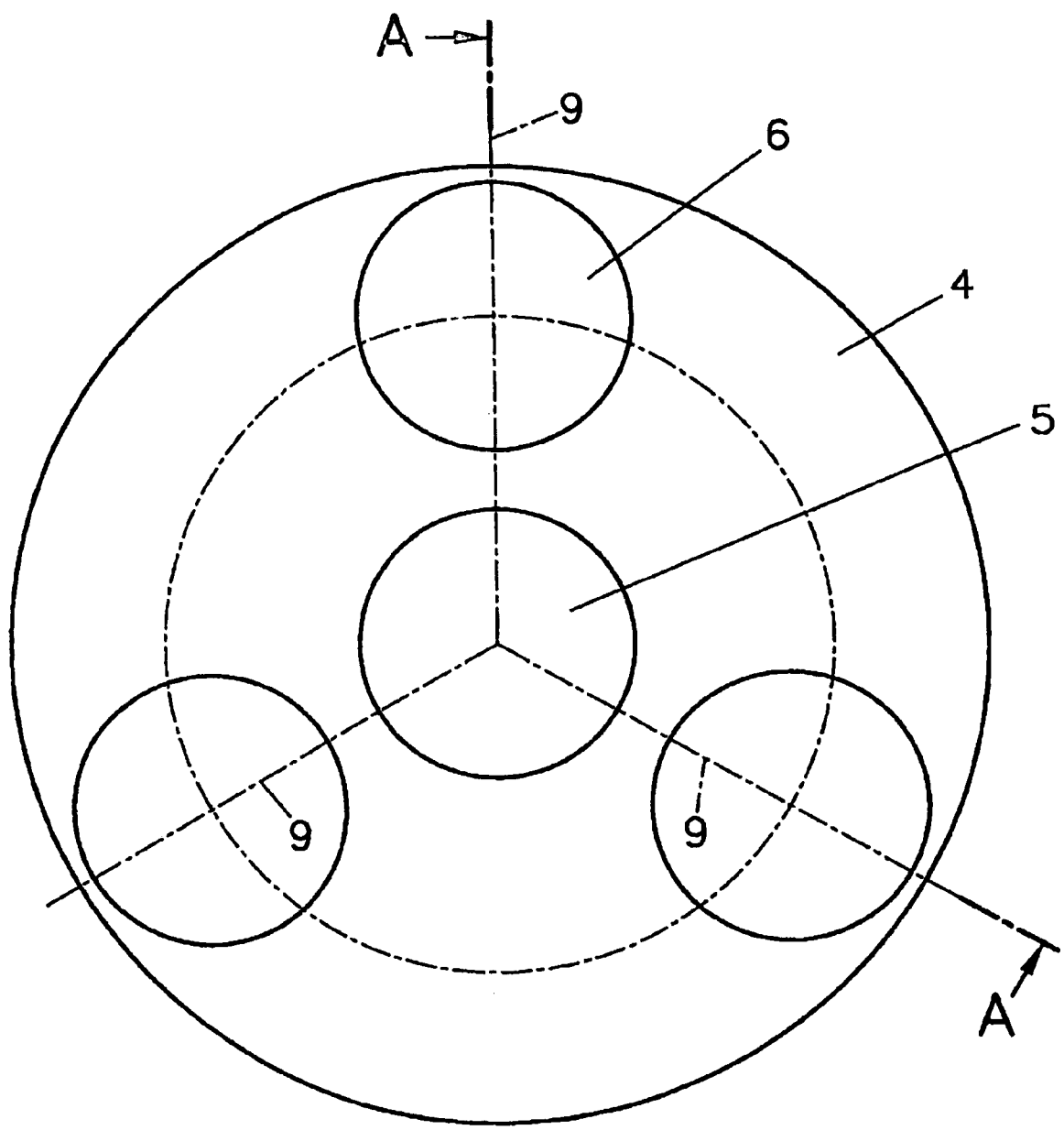
FIG. 1 shows a view of the rotor of an apparatus in accordance with the invention.
Figure 2:
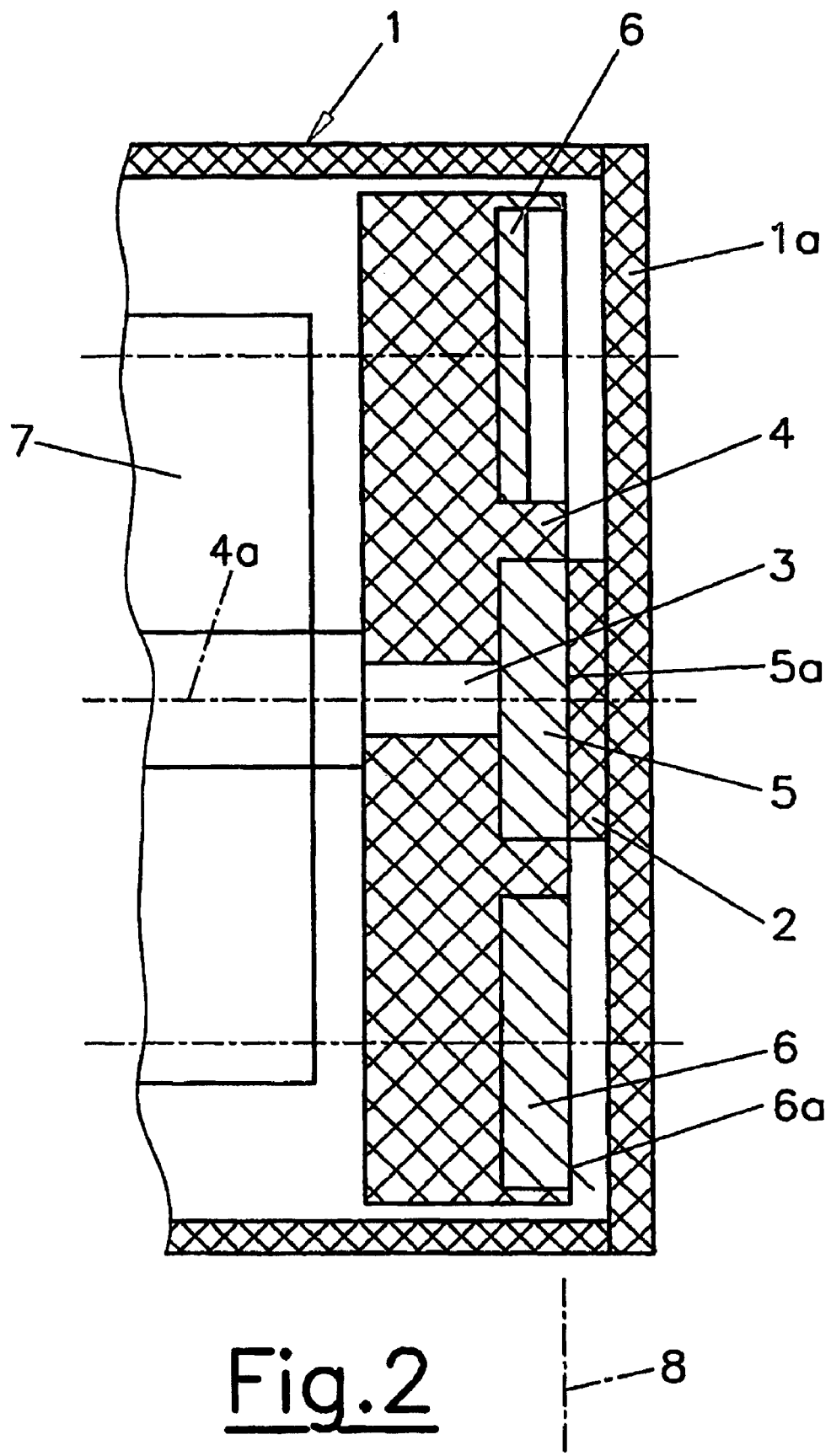
FIG. 2 shows a partial sectional view through an apparatus in accordance with the invention.

The apparatus of FIG. 1 consists of a housing 1 with a substantially plane housing wall 1a made of plastic. A rotor 4 is arranged in the housing 1, which rotor is rotatable about an axis 4a and is driven via a shaft 3 by a motor 7. A total of three circular first magnets 6 are arranged on the rotor 4 at angular distances of 120°. A stationary further magnet 5 is provided coaxially to the rotor 4, which magnet is rigidly connected with the first housing wall 1a via an intermediate plate 2. The front pole faces 6a of the first magnet 6 and the front pole faces 5a of the further magnet 5 lie in a common plane 8 which is arranged in the direct vicinity of the first housing wall 1a. The front pole faces 6a of the first magnets 6 each correspond to the magnetic north pole and the front pole face 5a of the further magnet 5 to the magnetic south pole. Respective control devices are not shown which allow a drive of the rotor 4 with different angular velocities and in changing directions of rotation.

Figure 3:
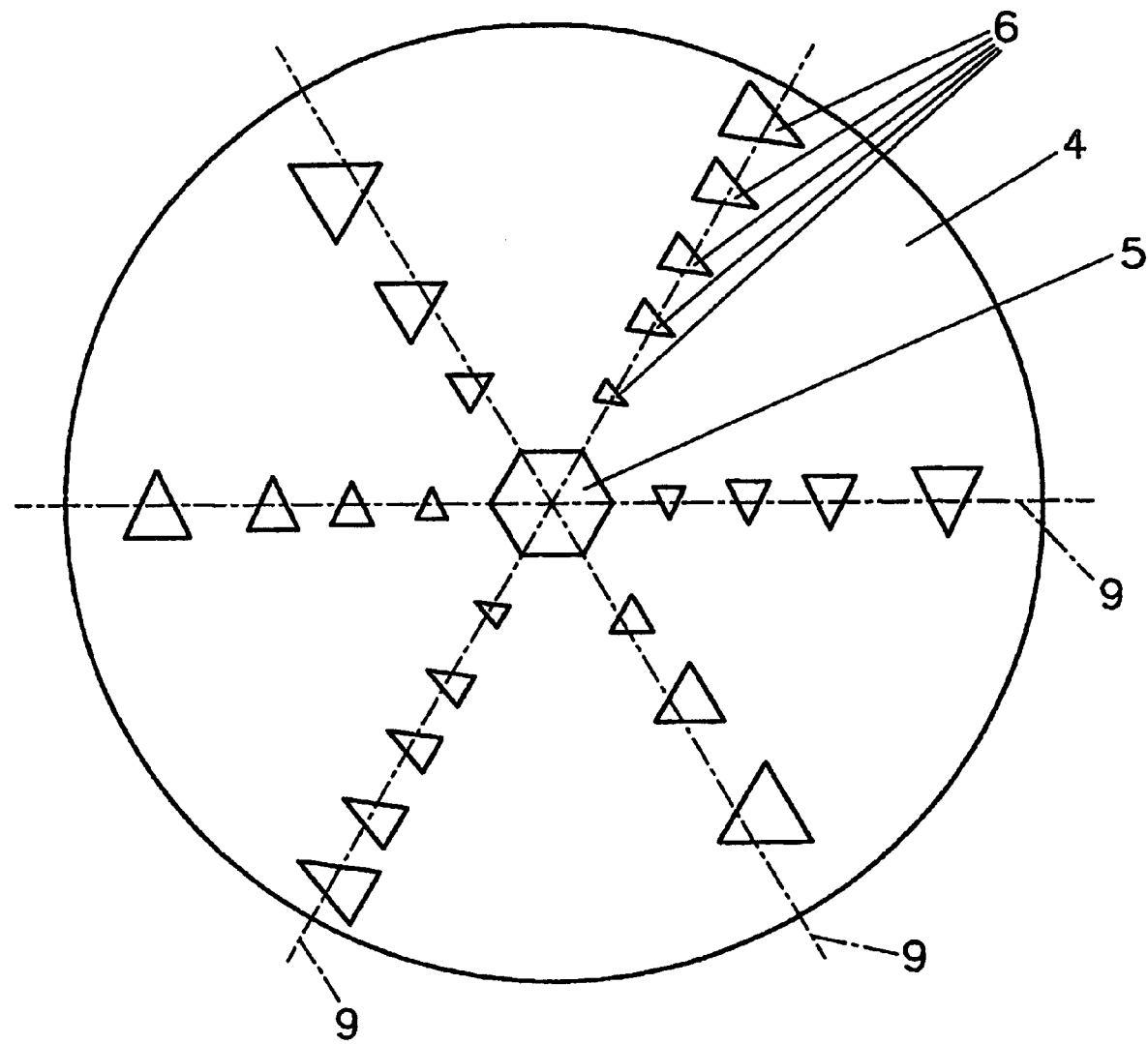
FIG. 3 shows a view according to FIG. 1 of an alternative embodiment of the invention.

An alternative embodiment is shown in FIG. 3 in which the first magnets are arranged on a total of six rays 9 in even angular distances of 60°, with several magnets 6 being arranged on each ray 9, of which there are five in the present case.

The invention claimed is:

1. An apparatus for detecting and influencing the physiological and/or pathological state of a human or animal body, comprising
a housing which includes a first housing wall having an outer surface for placing against the body to be treated,
a rotor inside the housing for rotation about a rotational axis which is essentially perpendicular to the first housing wall, said rotor having a plurality of first magnets mounted thereon along a plurality of radial rays and whose magnetic fields are oriented in the same direction which is parallel to the rotational axis, and a further magnet stationarily attached to the housing and substantially coaxially to the rotational axis, said further magnet being oriented to have an opposite polarity direction relative to the first magnets.

2. The apparatus according to claim 1, comprising three first magnets which are located on respective radial rays at 120° to each other.

3. The apparatus according to claim 1, wherein one first magnet is arranged along each ray.

4. The apparatus according to claim 1, wherein the first magnets and the further magnet comprise pole faces which lie in a common plane and are directly adjacent to the first housing wall.

5. The apparatus according to claim 1, including a drive motor for driving the rotor and which can be set to different speeds and rotational directions.

6. The apparatus according to claim 1, wherein the first magnets and the further magnet are permanent magnets.

7. The apparatus according to claim 1, wherein the first magnets and the further magnet are electromagnets.

8. The apparatus according to claim 1, wherein the further magnet is fixedly mounted on the first housing wall.

9. The apparatus according to claim 8, including a mounting plate between the further magnet and the first housing wall.

* * * * *